United States Patent [19]

Mahmoodian

[11] Patent Number: 4,924,857
[45] Date of Patent: May 15, 1990

[54] SURGICAL RETRACTOR

[76] Inventor: Saeed Mahmoodian, 204 Ridge Rd., Clarksburg, W. Va.

[21] Appl. No.: 288,899

[22] Filed: Dec. 23, 1988

[51] Int. Cl.$^5$ .............................................. A61B 17/02
[52] U.S. Cl. ...................................... 128/20; 128/345; 128/17
[58] Field of Search .................... 128/17, 18, 20, 345, 128/92 YC

[56] References Cited

U.S. PATENT DOCUMENTS

| 497,064 | 5/1893 | Van Meter | 128/20 |
|---|---|---|---|
| 2,693,795 | 11/1954 | Grieshaber . | |
| 3,384,077 | 5/1968 | Gauthier . | |
| 3,750,652 | 8/1973 | Sherwin . | |
| 4,156,424 | 5/1979 | Burgin . | |
| 4,300,541 | 11/1981 | Burgin . | |
| 4,344,420 | 8/1972 | Forder . | |
| 4,723,540 | 2/1988 | Gilmer, Jr. | 128/92 C |

FOREIGN PATENT DOCUMENTS 547292 3/1932 Fed. Rep. of Germany .
7333 5/1884 United Kingdom .

OTHER PUBLICATIONS

Journal de Chirurgie, vol. 42, Issue 3, Sep. 1933, p. 364.

Primary Examiner—Edward M. Coven
Assistant Examiner—Mark S. Graham
Attorney, Agent, or Firm—Armstrong, Nikaido, Marmelstein, Kubovcik & Murray

[57] ABSTRACT

A retractor for vaginal surgery having a pair of retractor blades centrally supported in a rectangualr frame formed by a pair of support bars to which the retractor blades are fixed, extending therefrom perpendicular to the plane of the frame. Adjustment of blade spacing is accomplished by turnbuckle mechanisms connecting the ends of the support bars and fixed thereto to maintain a substantially rectangular shape as the frame is adjusted.

4 Claims, 1 Drawing Sheet

U.S. Patent
May 15, 1990
4,924,857
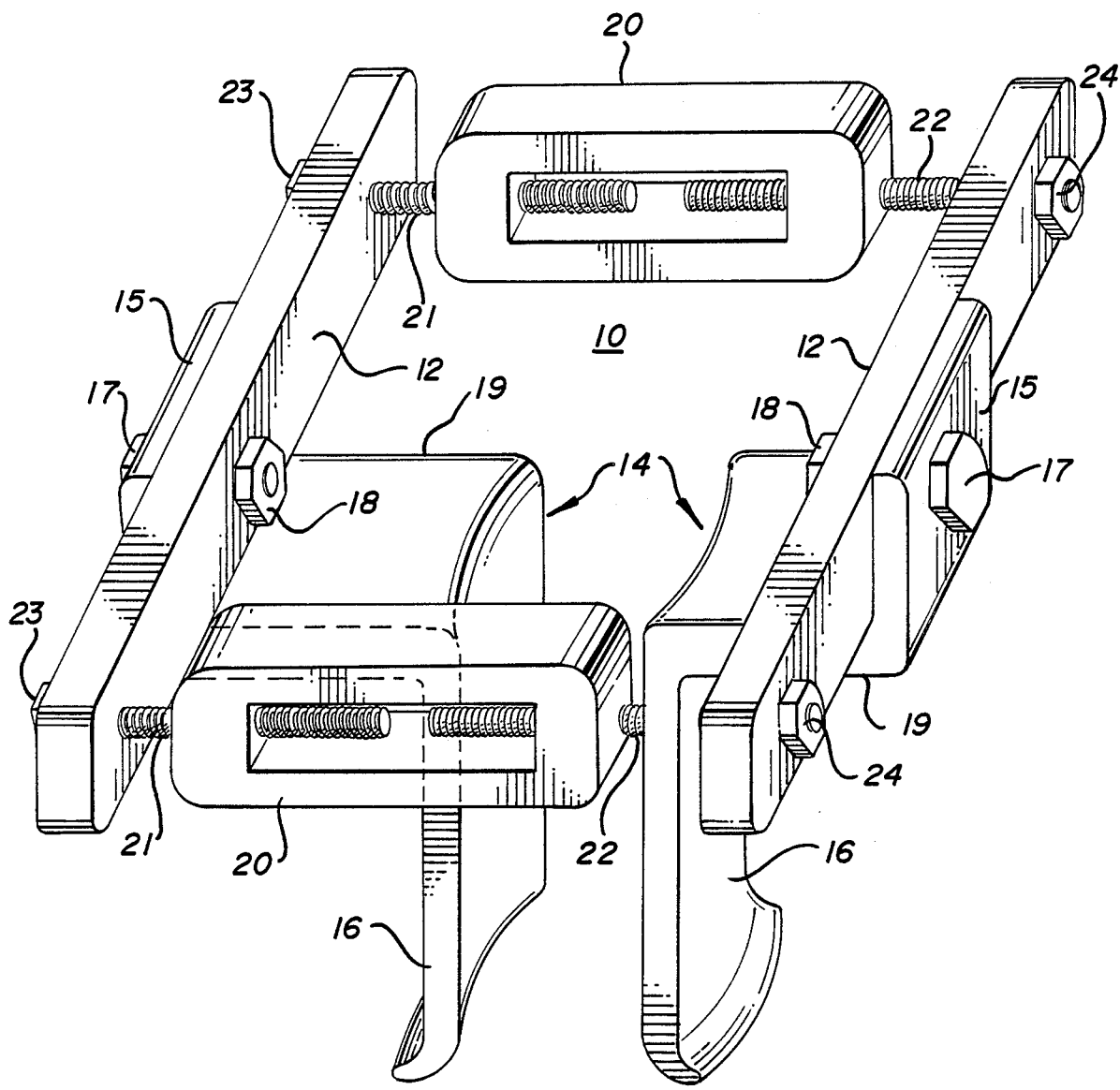

SURGICAL RETRACTOR

The present invention relates to a retractor for use in performing surgery, and more particularly to a retractor primarily useful for retraction of vaginal walls in the course of vaginal surgery. This device allows one doctor to perform surgery alone, which previously required services of an assistant to keep the walls separated.

SUMMARY OF THE INVENTION

The vaginal retractor of this invention comprises a pair of parallel supporting bars arranged in a frame so as to move toward and away from each other while maintaining their parallel relationship. The bars each support a retractor blade rigidly fixed thereto and extending perpendicular to the length of the supporting bar, the blades thereby being moved toward and away from each other by such movement of the supporting bars while being held parallel to each other in their longitudinal and lateral directions.

The relative movements of the bars and blades are accomplished by a pair of turnbuckle mechanisms connecting the ends of the bars. These mechanisms are composed of left- and right-threaded rods fixed to the ends of the rods and threaded into a sleeve so that rotation of the sleeve moves the rods in opposite directions.

BRIEF DESCRIPTION OF THE DRAWING

The single FIGURE shows a perspective view of a retractor device in accordance with the present invention.

DETAILED DESCRIPTION OF THE INVENTION

Referring to FIG. 1, the surgical retractor 10 shown therein comprises a pair of support bars 12 supporting a pair of retractor blades 14. The retractor blades each have an attachment portion 15 and a blade portion 16, the attachment portions being rigidly attached to a respective bar 12 by a screw 17 and nut 18. The blade portions 16 are curved slightly in their lateral dimension to form a generally cylindrically shaped surface along their length and also curved outwardly at their free ends.

Two turnbuckle mechanisms extend between the support bars perpendicular thereto and connect the support bars at their end portions. Each turnbuckle mechanism includes a sleeve 20 having a right-hand threaded rod 21 threaded thereinto at one end and a left-hand threaded rod 22 threaded thereinto at the other end. The threaded rods 21 and 22 may each be threaded into a hole having appropriate threads at the ends of bars 12, and locked to prevent rotation by lock nuts 23 and 24, respectively. The lock nuts may be positioned on the outside of the bars as shown, or on the inside of the bars. The rods may alternatively be fixed to the bars by any other means such as welding.

The retractor blades each include an offset portion 19 between the attachment portion and the blade portion which laterally displaces the blade portion 16 from the attachment portion 15 so that the blades, which extend at right angles to the frame formed by the support bars and the turnbuckle mechanisms, are centrally positioned between the support bars, allowing the blade portions to be moved together to meet each other. This facilitates insertion of the blades into the vagina. The retractor can then be opened wide for retraction by turning the turnbuckles.

The retractor frame always maintains a substantially rectangular shape during adjustment, and adjustment of the turnbuckle mechanisms moves the retractor blades in directions opposite to each other so that they do not become skewed. Because the turnbuckle mechanisms are positioned at the periphery of the operating area close to the hands of the surgeon, they may be reached quickly and easily to adjust the blade spacing during the course of an operation.

The rectangular frame formed by the support bars and the turnbuckle mechanisms, when opened to provide retraction, provides a wide space in the operating area without obstruction, while still providing convenient adjustment. Also, the outer portions of the frame are flat or gently rounded so that no sharp points are presented which might injure a patient in the event of uncontrolled movement during surgery.

This device provides a surgeon with a means to obtain retraction during vaginal surgery that has the advantage that it is convenient to use, provides a wide clear operating area, is easily adjustable and safe for a patient, and avoids the need for an assistent. The retractor may also be easily disassembled for cleaning and sterilizing.

What is claimed is:

1. A retractor for vaginal surgery comprising:
   a pair of support bars;
   a pair of retractor blades each including an attachment portion fixed rigidly to one of said support bars, said blades each also including a blade portion and an offset portion between said blade portion and said attachment portion;
   a pair of turnbuckle mechanisms, each having a central threaded link means, and a pair of oppositely threaded rods respectively rigidly fixed to said support bars at end portions thereof so as to form a frame;
   said retractor blades offset portions being formed such that said blade portions are laterally displaced from said support bars centrally of said frame, said blade portions extending at substantially right angles to the plane of said frame; and
   said support bars and retractor blades being moved toward and away from each other by adjustment of said threaded link means of said turnbuckle mechanisms, said frame maintaining a substantially rectangular configuration at all adjusted positions of said retractor blades.

2. A vaginal retractor comprising:
   a substantially planar rectangular frame formed by a pair of parallel support bars and a pair of turnbuckle mechanisms each having a central threaded link means and a pair of threaded rods respectively rigidly connected to said support bars at end portions thereof and extending at right angles thereto;
   a retractor blade fixed to each of said support bars at an intermediate portion thereof, said retractor blades each having an attachment portion rigidly attached to a support bar, a blade portion extending perpendicular to the plane of said frame, and an offset portion by which said blade portion is laterally displaced towards the center of said frame such that the blade portions can be moved to be adjacent to each other for insertion;
   adjustment of said threaded link means of said turnbuckle mechanisms serving to move said blade portions toward and away from each other while maintaining a parallel relationship of said blade portions and a substantially rectangular configuration of said frame.

3. A vaginal retractor as recited in claim 2, wherein said blade portions are formed to have facing cylindrically shaped surfaces.

4. A vaginal retractor as recited in claim 3, wherein free ends of said blade portions are outwardly curved.

* * * * *